United States Patent [19]

Inglefield, Jr. et al.

[11] 4,292,979

[45] Oct. 6, 1981

[54] ALLERGY TESTING APPARATUS

[76] Inventors: Joseph T. Inglefield, Jr., 210 E. Broad St., Falls Church, Va. 22046; William L. Mahood, 3404 Executive Ave., Falls Church, Va. 22042

[21] Appl. No.: 28,344

[22] Filed: Apr. 9, 1979

[51] Int. Cl.³ .............................................. A61B 10/00
[52] U.S. Cl. ..................................... 128/743; 128/253
[58] Field of Search .............................. 128/743, 253

[56] References Cited

U.S. PATENT DOCUMENTS

| | | | |
|---|---|---|---|
| 2,301,567 | 11/1942 | Morse | 128/743 |
| 2,522,309 | 9/1950 | Simon | 128/743 |
| 3,289,670 | 12/1966 | Krug et al. | 128/743 |
| 3,444,989 | 5/1969 | Hertel et al. | 128/253 X |
| 3,556,080 | 1/1971 | Hein | 128/743 |
| 3,675,766 | 7/1972 | Rosenthal | 128/253 X |
| 3,894,531 | 7/1975 | Saunders | 128/743 |

FOREIGN PATENT DOCUMENTS 209624 7/1968 U.S.S.R. .............................. 128/743

Primary Examiner—Kyle L. Howell
Attorney, Agent, or Firm—Lane, Aitken, Ziems, Kice & Kananen

[57] ABSTRACT

Allergy testing apparatus for conveniently and quickly testing a subject's reactions to a plurality of allergens. The apparatus includes needle blocks, cover apparatuses including a layer of closed-cell foam having a smooth skin, and apparatus for removably holding a plurality of allergen containing vials for cooperation with the needle blocks and the cover apparatuses. In use, closure of the vials may be effected by the cover apparatus of the needle block, and the respective allergen containing vials are maintained in an uncontaminated condition.

13 Claims, 5 Drawing Figures

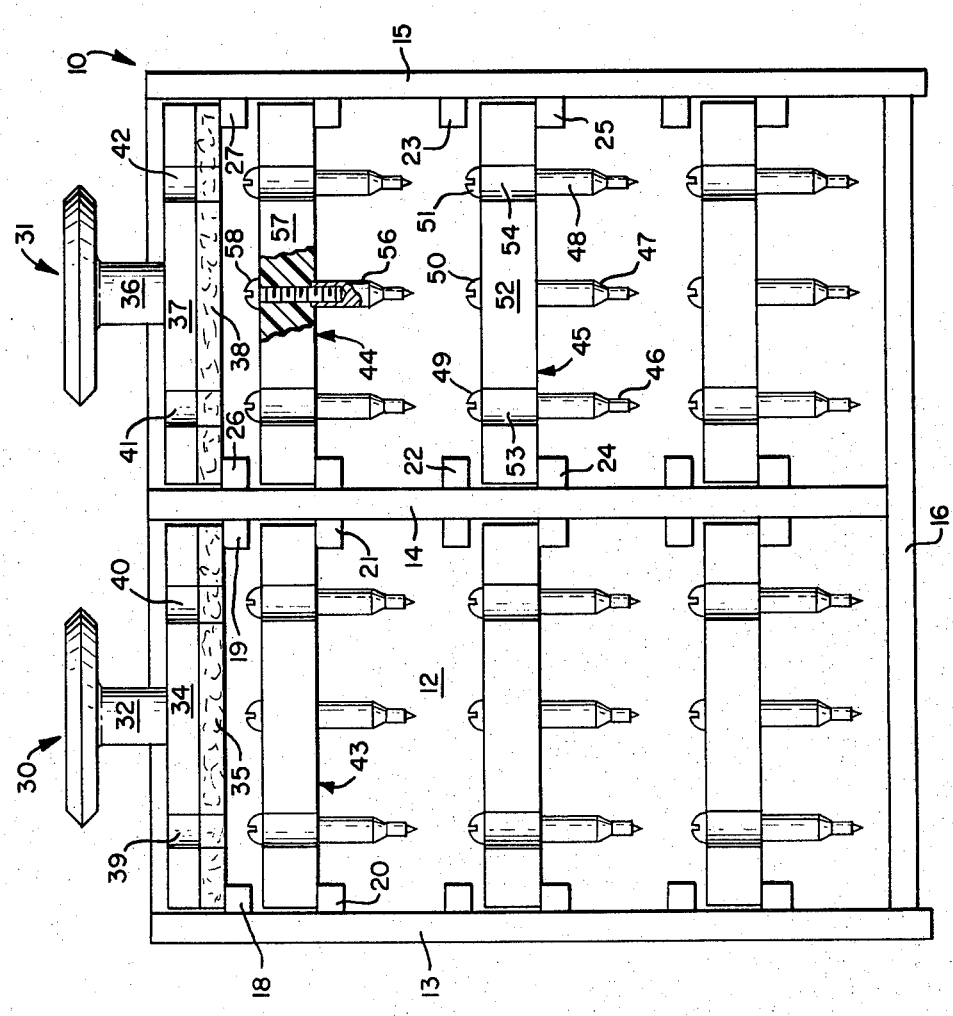

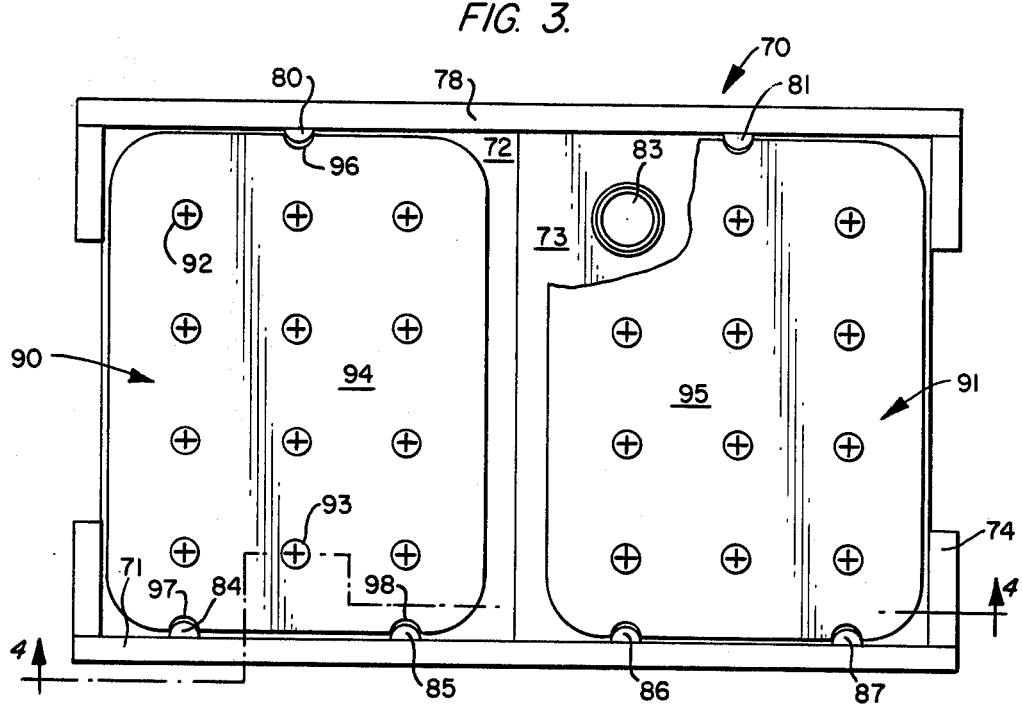
FIG. 3.
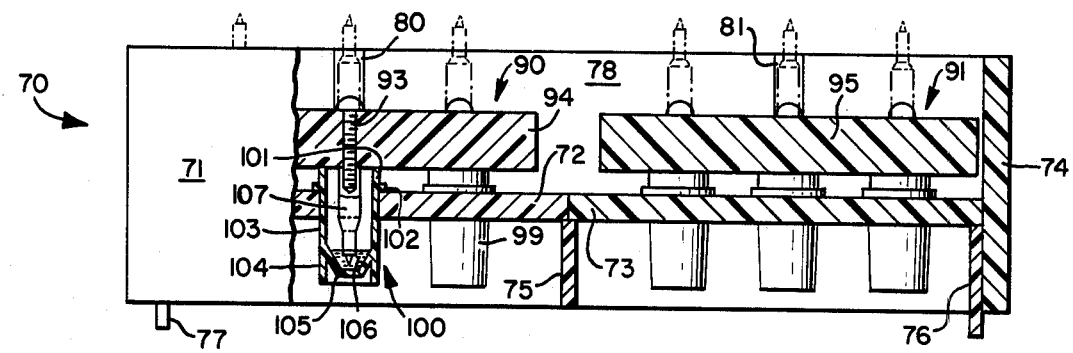
FIG. 4.
FIG. 5.

ALLERGY TESTING APPARATUS

BACKGROUND OF THE INVENTION

This invention relates to allergy testing and, more particularly, to an improved apparatus for testing the reaction to a relatively large number of allergens simultaneously.

It has been proposed in the past to test reactions to several allergens simultaneously. These systems have involved mounting several needles on a common base or needle block in a parallel arrangement. An allergen container is provided having a plurality of wells defined in a block, each well being positioned so that each can have inserted therein a separate needle from the mounted set. Each well is partially filled with a different allergen and the needles are inserted into the wells, dipped into the contained allergens, and then simultaneously applied to the skin of the subject. These systems of the prior art, while greatly improving over the conventional technique of using one allergen needle at a time, are still relatively inconvenient and expensive procedures.

SUMMARY OF THE INVENTION

The system of the present invention, like those of the prior art, employs needles mounted on bases for simultaneous dipping into allergens. However, the system of the present invention improves on the prior art systems by providing a separable, replaceable vial to contain each allergen. The vails are supported in a holder which positions the vials to receive the needles simultaneously. The vials are assembled in a holder in two sets designed to receive a battery of needles on a separate needle block. Two lids are provided, each operable to one set of vials. Each lid is provided with a layer of closed-cell foam having a smooth skin adapted to contact the mouths of the vials and maintain closure thereof. The lids or covers, like the needle sets, are keyed to the holders so that each lid can be placed on the holder only in one position so the lids cannot serve as carriers to transmit allergen from one vial to another. The vial holders and the lids are color keyed to one another to facilitate assuring that the same cover is always received in the same set of vials and the same lid is always placed on the same set of vials. The mounted needle sets or needle blocks are designed to be steam sterilized in an autoclave where each of the needle sets may be stored. The lids, when not in place on the vial holder, are stored on a shelf which holds the foam layer out of contact with any surface.

The vials with the desired set of allergens are assembled in the holder and stored in a refrigerator with the lids in place closing the vials. To use the system, the lids are removed and placed on the shelf, and the needle sets are inserted into the vials, each needle entering a separate vial and being dipped in a separate allergen. The holders with the needle sets in place may then be taken to the subject of the allergy test and the needle sets applied to the subject, each needle simultaneously injecting the allergen in the skin of the subject. After application, the needle sets are replaced on the holder with the needles facing outwardly, the back side of the block member of each needle block thereby forming a closure member for the vials.

The site of each needle puncture on the subject may be observed for the reaction of the applied allergen. In this manner, the subject's reaction to twenty-four allergens may be tested at one time. Following the test, the holder with the needle sets in position upside down are taken back to the laboratory where the needle sets are removed, cleaned and placed in the autoclave for sterilization and the lids replaced on the holders to close the individual vials.

Because separate replaceable vials are employed to contain the allergens, the allergens of the test can be easily varied in any desired combination with minimum waste of the allergens. Because the lids maintain the vials closed for storage, the same vials can be used again for tests on other subjects without having to repeat the procedure of placing allergens in containers to receive the needle sets. The allergens in the vials can be repeatedly used on different subjects without danger of infection or contamination because of the sterile conditions of the needles on each needle block prior to each test. Thus, the test of twenty-four allergens can be carried out repeatedly, quickly and conveniently on separate test subjects.

Further objects and advantages of the invention will become apparent in the following detailed description of the invention.

BRIEF DESCRIPTION OF THE DRAWINGS

FIG. 1 is a front elevation, partially fragmentary, of apparatus for holding two allergen-vial-cover apparatuses and six allergen-testing-needle blocks ready for use;

FIG. 2 is a side elevation, partially fragmentary, of the apparatus of FIG. 1;

FIG. 3 is a plan view of apparatus for holding two sets of allergen vials, with two allergen-testing-needle blocks inserted thereon;

FIG. 4 is a view taken along line 4—4 of FIG. 3 illustrating further details of the apparatus, and also showing an alternative inverted position for the needle blocks; and FIG. 5 is a view similar to FIG. 4 but showing the allergen-vial-cover apparatuses in place over the allergen-containing vials.

DESCRIPTION OF THE PREFERRED EMBODIMENTS

As shown in FIGS. 1 and 2, a cabinet apparatus 10 is provided for holding various components comprising the allergen-testing apparatus of the present invention. The cabinet 10 preferably is used to hold such components when they are not actually being utilized for allergen testing or at times preparatory to actual use for allergen testing.

The cabinet 10 is an open-top-type cabinet having two side members 13 and 15, a bottom member 16, and back member 12, and a center-divider member 14.

The cabinet 10 is adapted to support and hold two allergen-vial-cover apparatuses 30 and 31 positioned therein by means of support members 18, 19, 26 and 27 as shown. The support member 18, for example, extends horizontally along the inside of the side wall member 13 and the support member 19 extends horizontally along one side of the center-divider member 14 so that the two support members 18 and 19 effectively form a partial shelf. The support members 26 and 27 are similarly attached to the center-divider member 14 and the inside wall of the side member 15, respectively, to provide a partial shelf to support the cover apparatus 31.

The two allergen-vial-covering apparatuses 30 and 31 shown in FIG. 1 are the same. The cover apparatus 30 includes a handle member 32 attached to a plate-like member 34. A layer of closed-cell foam 35 having a smooth skin is attached to the member 34. Two key slots 39 and 40 are formed in an edge at one end of the cover apparatus 30 and are adapted to cooperate with key members to be further described. Similarly, the cover apparatus 31 includes a handle member 36 attached to a plate-like member 37 to which is attached a layer of closed-cell foam 38 having a smooth skin. Two key-slot grooves 41 and 42 are similarly formed in an edge at one end of the cover apparatus 31.

The cabinet 10 also includes means for supporting a plurality (six as disclosed in FIG. 1) of allergen testing needle blocks such as the needle blocks labelled with numerals 43, 44 and 45. Each of these needle blocks has the same construction.

The needle block 43, for example, is adapted to be supported on a partial shelf formed by two support members 20 and 21. The support member 20 extends horizontally along the inner surface of the wide wall member 13, and the support member 21 extends horizontally along one surface of the center-divider member 14 to form a partial shelf. It is noted that the two support members 18 and 19 previously described also form upper confining members for the needle block 3 and effectively contain the needle-block member 43 between the support members 18 and 20 and 19 and 21 when the needle block 43 is positioned and stored in the cabinet 10 as shown in FIG. 1.

In operation, the needle block 43 may be slid in and out of the cabinet 10 to be supported from below by the support members 20 and 21 and to be contained from above by the lower surfaces of the support members 18 and 19. Similarly, the cover apparatus 30 may be either slid in from the side to rest on the support members 18 and 19 or may, alternatively, be positioned on the support members 18 and 19 by insertion from the open top of the cabinet 10. When thus stored, the foam layer 35 of the cover apparatus 30 is maintained out of contact with any other surfaces.

A partial-fragmentary view is shown of the needle block member 44 and illustrates the means preferably employed for attachment of the plurality of needle members such as the needle member 56 to a block member such as the block member 57. The block member 57 of the needle block 44 preferably is made of a transparent, sterilizable material. A plurality of needle members such as the needle member 56 are attached to the needle block member 57 by means of a plurality of machine screws such as the machine screw 58 which is adapted to be inserted through a throughbore through the block member 57 and threaded into internal threads in the needle member 56 to attach the needle member 56 firmly to the block member 57 as shown. Alternatively, the machine screws such as the machine screw 58 could be embedded in the block member 57 with the threaded portion thereof extending out of the block member so that the needle member 56 could be threaded thereon. In either case, the various needle members are selectively removable. The needles 56 as shown in FIG. 1 have a specially shaped point to preserve sharpness. The needle has a shoulder surrounding the point which regulates the depth of penetration into the skin of the test subject. This facilitates uniformity in conducting and interpreting the test. Further, the combined shape of the shoulder and point holds a minimal and precise amount of allergen liquid by surface tension.

Preferably, each of the plurality of needle members in each needle block is attached on one side of each block member in this manner, although other attachment means may be employed. For example, the needle block 45, in the front elevation view of FIG. 1, is shown as having three needle members 46, 47, and 48, each of which is fastened to one side of a block member 52 by means of cooperating machine screws 49, 50 and 51, respectively. The needle-block member 52, when the needle block 45 is stored in the cabinet 10, is supported from below by two horizontally-extending-support members 24 and 25 attached, respectively, to the cabinet 10, and contained from above by two horizontally-extending-containment members 22 and 23 also attached to the cabinet 10 as shown. When thus stored, the needle members are maintained out of contact with any other surfaces. The needle block 45, as in the case of the other needle blocks 43, 44, etc. shown in FIG. 1, includes two key slots 53 and 54 which are adapted to cooperate with certain key members when the apparatus is used for allergen testing as will be further described.

The view of FIG. 2 shows several additional structural features of the apparatus already described with particular reference to FIG. 1. A screw member 33 may, for example, be used to fasten the handle member 36 of the cover apparatus 31 to the related plate member 37. The foam layer 38 of the cover apparatus 31 may also, for example, be fastened to the plate member 37 by an adhesive or epoxy. It is similary seen in FIG. 2 that the needle block 45 also includes a single key slot 55 on the rear edge thereof. This key slot is adapted to cooperate with a key member when the apparatus is used as will be further described. It is also shown in the fragmentary side elevation of FIG. 2 that the needle block 45 contains a plurality of needle members extending downwardly. In a preferred embodiment, as will be further described, each needle-block member preferably includes a total of twelve (12) needle members arranged in four rows with three needle members in each row.

As shown in FIG. 3, two needle-block members 90 and 91 are shown positioned in plan view on an allergen-vial-holding apparatus 70 with the needle members facing downwardly into the vials. The allergen-vial-holding apparatus 70 includes a front member 71, a rear member 78, and side members including a partial side member 74 as shown. Two plate-like members 72 and 73, each containing a plurality of apertures therein adapted each to removably receive and hold an allergen-containing vial, such as an allergen vial 83, extend between the side wall members and the front and rear members 71 and 78 of the apparatus 70 as shown. A vertically-aligned, horizontally-extending vertical-support member 75 also extends between the front and rear members 71 and 78 and supports the two plate-like members 72 and 73 on the common adjoining edges thereof. Similarly, two vertically-aligned, horizontally-extending members 76 and 77 are attached to the internal side walls of the apparatus 70 to provide supports for the plate-like members 73 and 72, respectively, and also to provide supporting "feet" for the apparatus 70 when it is positioned, for example, on a horizontally-aligned, planar surface. The configuration allows units to nest one above the other for storage.

The apparatus 70 also includes a plurality of key members 80, 81, 84, 85, 86, and 87 adapted to cooperate with the key slots provided on the needle blocks 90 and 91 with the corresponding key slots provided on the cover apparatuses such as 30 and 31.

The needle block 90 includes a block member 94, preferably constructed of a transparent, sterilizable material as previously described. As shown in the plan view of FIG. 3, a plurality of Phillips-head-machine screws, such as machine screws 92 and 93, are arranged in four rows with three screws in each row. Each of these machine screws cooperates with a needle member (not shown in view of FIG. 3) and attaches the related needle member to the underside of the block member 94. The block member 94 also includes on one edge thereof, a single key slot 96 adapted to cooperate with the key member 80 of the apparatus 70. Two key slots 97 and 98 are similarly formed or provided on the opposite edge of the block member 94 and are adapted to cooperate with the key members 84 and 85, respectively, of the vial-holding apparatus 70.

Similarly, the needle block 91 includes a block member 95 having key slots formed therein to cooperate with the respective key members 81, 86, and 87 as shown. The allergen-containing vial 83 is also shown removably received and held in position in an aperture formed in the plate member 73. As will be further described with reference to FIGS. 4 and 5, the vial holding apparatus 70 is adapted to hold a plurality of single allergen-containing vials, each positioned under a separate needle member of each needle block 90 and 91 when those needle blocks are received onto the apparatus 70 with the key members and slots aligned as shown and with the needle members facing downwardly as shown.

As shown in FIG. 4, a plurality of allergen-containing vials, such as vials 99 and 100, are removably received and held in respective apertures formed in the plate members 72 and 73 of the apparatus 70. These vials (and the related apertures) are positioned for alignment under the respective needle members of the needle blocks 90 and 91 when the needle blocks are received on the apparatus 70 with the key slots aligned with the key members and the needle members facing downwardly as shown. For example, the block member 94 of the needle block 90 has an aperture formed therethrough to receive therein the machine screw 93 which is threaded into the needle member 107, which extends into the interior portion of the vial 100 so that, in operation, the needle point of the needle member 107 is positioned or "dipped" in a liquid allergen 106 contained in the lower-interior portion of the vial 100 as shown in FIG. 4.

All vials are preferably the same as the vial 100 and each is preferably made of a partially-resilient, plastic material so that each vial may be removably inserted through the apertures formed in the plate-like members 72 and 73 to permit changing of the allergens used for testing or replacement of each vial. The vials are disposable so as to avoid contamination resulting from allergen being absorbed in the wall of a used vial. The vial 100 has a cylindrical-upper-wall member 101 having a flange 102 formed thereon. The circular flange 102 permits the vial 100 to be supported on the plate member 72 when partially inserted into the aperture formed in the plate member 72 to receive the vial 100. The vial 100 also includes a central-cylindrical-wall member 103 which includes a cylindrical-wall portion 104 which extends below a bottom member 105 which forms a closed generally conically-shaped-lower cavity in the vial 100 which is adapted to hold the liquid allergen 106 as shown in FIG. 4. This shape for the interior cavity permits effective "dipping" of the needle members into allergens with a minimum amount of liquid allergen being required.

To facilitate insertion and removal of each vial, a slight taper may be provided in the outside diameter of each vial, with the lower portion of each vial having the smaller diameter. Each vial may also be separately marked or colorcoded for easy visual identification of different allergens used therein. Separate caps or lids (not shown) may be provided for each vial when not being used in the apparatus 70.

FIG. 4 also illustrates with broken lines, the needle blocks 90 and 91 in an alternative position in which the needle members are directed upwardly which will be further described. In actual use of the apparatus of FIGS. 3-5, each needle block is first inserted onto the apparatus 70 with the key members and key slots aligned and with the needle members facing downwardly so that each needle member is dipped into an allergen in the particular vial aligned therewith. Each needle block, with the allergens thus received on each needle member, are then used for allergen testing of the skin of the subject or patient. After application to the patient, the needle blocks may then be replaced on the apparatus 70 with the key members and key slots aligned and with the needle members facing upwardly as shown in the alternative position in FIG. 4. In this alternative position, the planar surface of the block members is received against the upper portions (for example, portion 101 of the vial 100) of the vials to form an upper-closure surface for the vials.

Alternatively, the vial-cover apparatuses 110 and 115 corresponding indentically to the vial-cover apparatus 30 and 31 of FIG. 1 may be used to achieve vial covering and closure. For example, the vial-cover member 110 includes a handle member 111 attached to a plate-like member 112 to which is attached a layer of closed-cell foam material having a smooth skin 113. When the cover member 110 is positioned over the vials, for example, over the allergen containing vials 100 and 99 in FIG. 5, closure is achieved to prevent evaporation or contamination of the allergens contained therein. The key slots formed in the edge of the covering apparatus (such as elements 30, 31, 110, 115) must be aligned with the key members on the apparatus 70. The plate members 72 and 73 are made of different colored material for reference identification of the set of allergens. The plate-like member 112 of the vial-cover member 110 is also colored so that covers and vial-holder plates are colored keyed to each other.

The method of using the apparatus is fully described in the "Summary of the Invention".

Accordingly, it is seen that the apparatus of the present invention permits a subject's reaction to up to twenty-four (24) allergens to be tested at one time by utilizing different allergens in each of the twenty-four (24) vials provided in the holding apparatus 70. A separate needle block with twelve (12) needle members is, of course, used for each set of twelve (12) vials in the apparatus 70 to prevent transmission of different allergens from one vial to another. Following each test, the needle blocks are preferably again positioned on the apparatus 70 but with the needle members facing upwardly. With this arrangement, the planar surfaces of the block members of the needle blocks serve as temporary closure members closing off each vial, thereby preventing contamination of the allergens contained in each vial as the apparatus 70 is taken back to the laboratory where, for example, the needle blocks are removed, cleaned and placed in, for example, an antoclave, for re-sterilization. When the needle blocks are removed from the apparatus 70 for re-sterilization, the vial-cover apparatuses are used for closing off each vial to prevent evaporation, contamination, etc., during subsequent storage.

Because separate replaceable vials are employed to contain the allergens, the set of allergens used in any particular test may be easily varied in any desired combination with most efficient use of allergens. Because the vials are closed off during storage to prevent evaporation, contamination, etc., the same vials containing the same allergens may be reused for tests on different subjects without having to repeat the procedure of placing new allergens in new vials. Because of the construction of the vial-cover apparatus which closes all of the vials simultaneously, the entire procedure of using the apparatus starting with removing the apparatus from storage, then opening the vials, performing the allergy test, closing the vials, and returning the apparatus to storage can be carried out quickly, easily and conveniently. The allergens in the vials can be repeatedly used on different subjects without danber of infection or contamination because sterile conditions exist for each needle block prior to each test. Thus tests of up to 24 allergens can be carried out repeatedly, quickly and conveniently on different test subjects.

Accordingly, it is seen that the apparatus of the present invention achieves the foregoing objectives as well as other objectives which will be apparent to those skilled in the art. It will, of course, be apparent to those skilled in the art that various changes and modifications may be made to the apparatus of the present invention without departing from the scope of the invention as defined in the appended claims.

What is claimed is:
1. Allergy-testing apparatus comprising:
a needle block comprising a block member having a plurality of separately-located-needle members extending from one side thereof, each of said needle members having a point on the distal end thereof;
vial-holding apparatus comprising a planar-plate member with a plurality of apertures formed therein, each aperture holding a single removable vial adapted to hold a liquid allergen; said apertures being positioned so that if said needle block is inserted on said holding apparatus with said one side of said block member facing said holding apparatus, then each of said needle members is separately received in a vial held in said plate member.

2. Allergy-testing apparatus according to claim 1 further comprising a vial-cover apparatus including a planar layer of closed-cell foam having a smooth skin adapted to serve as a closure means for the vials received in said apertures when said needle block is not inserted on said holding apparatus.

3. Allergy-testing apparatus according to claim 1 further comprising key slots formed in the edge of said block member, and key members positioned near the edges of said plate member; said key slots and key members being adapted for cooperative engagement when said needle block is inserted on said holding apparatus.

4. Allergy-testing apparatus according to claim 2 further comprising a cabinet apparatus including a plurality of partial-shelf means therein; at least one of said partial-shelf means being adapted to support said vial-cover apparatus such that the area of said foam layer which engages said vials is maintained out of contact with any surface; a plurality of said partial-shelf means being adapted to each separately support said needle block such that said needle members are maintained out of contact with any surface.

5. Allergy-testing apparatus according to claim 2, wherein said vial-cover apparatus further includes a plate member, said layer of foam being adhered thereto and having key slots formed in the edges thereof, said key slots of said vial-cover apparatus being adapted for cooperative engagement with key members on said vial-holding apparatus.

6. Allergy-testing apparatus according to claim 3 further comprising a vial-cover apparatus including a plate member having key slots formed in the edges thereof, a planar layer of closed-cell foam having a smooth surface adhered to said plate member of said vial-cover apparatus, said vial-cover apparatus being adapted to serve as a closure means for the vials received in said apertures when said needle block is not inserted on said holding apparatus, said key slots of said vial-cover apparatus being adapted for cooperative engagement with said key members.

7. Allergy-testing apparatus according to claim 1, wherein said block member includes a transparent material which is sterilizable by autoclave and wherein said needle members are removably attached to said block member by machine screws.

8. Allergy-testing apparatus according to claim 1, wherein each of said vials includes a cylindrical-wall member; a circular flange extending outwardly of said cylindrical wall member, the lower surface of said flange being adapted to rest on the upper surface of said plate member of said holding apparatus when said cylindrical-wall member is inserted into one of said apertures; and a bottom-closure member defining a conically-shaped bottom cavity for said vial.

9. Allergy-testing apparatus according to claim 1, wherein the other side of said needle block from that on which said needle members are attached is planar and will operate to cover said vials when said needle block is inserted on said holding apparatus with said other side of said block facing said holding apparatus.

10. A method of allergy testing of a subject's reactions to a plurality of allergens comprising the steps of:
positioning a plurality of removable vials, each containing a specific allergen, in predetermined apertures formed in a plate member of a vial holding apparatus;
inserting a needle block having a plurality of sterile needle members attached thereto on one side thereof onto said vial-holding apparatus so that said needle members are separately dipped into allergens contained in said vials;
removing said needle block from insertion on said vial-holding apparatus;
applying said needle block to the skin of the subject such that the needle members dipped in allergen puncture the skin of the subject to a controlled depth; and
inserting said needle block onto said vial-holding apparatus so that said needle members face in a direction away from said vials, the surface of said needle block thereby serving as a closure means for said vials.

11. A method according to claim 10 further comprising, after the last step recited in claim 10, the futher steps of:
removing said needle block from said vial-holding apparatus;
inserting a vial-cover apparatus having a plate member and having a planar layer of closed-cell foam having a smooth skin onto said vial-holding apparatus so that said smooth skin surface of the foam layer serves as a closure means for said vials; and
sterilizing the needle members of said needle block.

12. A method according to claim 10 further comprising, after the last step recited in claim 10, the further steps, to test a second subject's reactions to a plurality of allergens, of:
removing the used needle block from said vial-holding apparatus;
inserting a second sterile needle block having a plurality of sterile needle members attached thereto on one side thereof onto said vial-holding apparatus so that said needle members are separately dipped into allergens contained in said vials positioned in said vial-holding apparatus;
removing said second needle block from insertion on said vial-holding apparatus; and
applying said second needle block to the skin of the second subject such that the needle members dipped in allergen puncture the skin of the subject to a controlled depth.

13. An allergy-testing apparatus comprising:
first and second needle blocks each comprising a block member having a plurality of separately located needle members removably attached to one side thereof;
a vial-holding apparatus comprising first and second planar-plate members of different colors, each of said plate members having a plurality of apertures formed therein, each aperture holding a removable single vial adapted to hold a liquid allergen;
said apertures being positioned so that said first and second needle blocks can be inserted simultaneously on said holding apparatus with one side of the block members facing said holding apparatus and each of the needle members of said first needle block being separately received in a vial held in said first plate member and each of the needle members of said second needle block being separately received in the vials held in said second plate member;
first and second vial-cover apparatuses each having a different color corresponding to the colors of said plate members, each of said cover apparatuses including a planar layer of closed-cell foam having a smooth skin and adapted to serve as an airtight closure means for the vials received in the apertures of the plate member of the corresponding color when said needle block is not inserted on said holding apparatus.

* * * * *